United States Patent
Sakamoto et al.

(10) Patent No.: US 6,681,620 B2
(45) Date of Patent: *Jan. 27, 2004

(54) VEHICLE PERFORMANCE EVALUATION TEST METHOD AND APPARATUS

(75) Inventors: Shigeru Sakamoto, Susono (JP); Junichi Takeda, Okazaki (JP); Norihiko Okochi, Aichi-gun (JP); Tetsuya Ogawa, Susono (JP); Osamu Takenaka, Kariya (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 25 days.

This patent is subject to a terminal disclaimer.

(21) Appl. No.: 10/096,134

(22) Filed: Mar. 11, 2002

(65) Prior Publication Data
US 2002/0134168 A1 Sep. 26, 2002

(30) Foreign Application Priority Data
Mar. 23, 2001 (JP) ........................ 2001-085525

(51) Int. Cl.[7] ................................ G01L 5/28
(52) U.S. Cl. ...................................... 73/132
(58) Field of Search .................. 73/132, 121, 40, 73/126; 701/70, 76; 180/273; 60/245; 123/204.23; 303/113.2, 3

(56) References Cited

U.S. PATENT DOCUMENTS

| | | | | | |
|---|---|---|---|---|---|
| 3,662,593 A | * | 5/1972 | Pirrello et al. | ................ | 73/132 |
| 3,722,266 A | * | 3/1973 | Dunham | ................ | 73/132 |
| 3,977,241 A | * | 8/1976 | Asmus et al. | ................ | 73/132 |
| 5,230,549 A | * | 7/1993 | Osada et al. | ................ | 303/3 |
| 5,483,825 A | * | 1/1996 | Greenbaum | ................ | 73/132 |
| 6,126,246 A | * | 10/2000 | Decker, Sr. et al. | ........... | 303/7 |

FOREIGN PATENT DOCUMENTS

| JP | 56-169247 | 12/1981 |
|---|---|---|
| JP | A 11-132914 | 5/1999 |

* cited by examiner

*Primary Examiner*—Edward Lefkowitz
*Assistant Examiner*—Octavia Davis
(74) *Attorney, Agent, or Firm*—Oliff & Berridge, PLC

(57) ABSTRACT

A method and apparatus for conducting a vehicle performance evaluation test by automatically depressing a control member of the vehicle to be depressed by a vehicle operator uses an actuator of a vehicle performance evaluation test apparatus. The actuator depresses the control member, the actuator having a first end and a second end. The first end of the actuator is fixed to a seat of the vehicle. The second end of the actuator is engaged with the control member of the vehicle. The actuator is caused to exert a depressing force to depress the control member relative to the seat so as to automatically depress the control member.

32 Claims, 7 Drawing Sheets

VEHICLE PERFORMANCE EVALUATION TEST METHOD AND APPARATUS

INCORPORATION BY REFERENCE

The disclosure of Japanese Patent Application No.2001-085525 filed on Mar. 23, 2001, including the specification, drawings and abstract is incorporated herein by reference in its entirety.

BACKGROUND OF THE INVENTION

1. Field of Invention

The invention relates to a vehicle performance evaluation test method and apparatus, and more particularly to a vehicle performance evaluation test method and apparatus for evaluating a vehicle performance using a pressing device (an actuator) that automatically applies a depressing force to a control member to be operated by a vehicle operator.

2. Description of Related Art

In order to conduct a test for evaluating a braking performance such as a braking distance and deceleration of a vehicle, for example, a motor vehicle, a brake pedal needs to be depressed with a predetermined pressing force or the brake pedal needs to be depressed so as to achieve a predetermined deceleration while keeping the vehicle in a running state. It is, however, difficult for the vehicle operator to accurately operate the brake pedal as described above.

JP-A-11-132914 discloses a vehicle performance evaluation test apparatus that automatically operates the brake pedal for the vehicle operator. The test apparatus is fixedly set under the seat of the vehicle and provided with a control rod which extends in a longitudinal direction of the vehicle and a driving mechanism which drives the control rod forward and backward. The control rod serves to automatically operate the brake pedal with its tip such that the performance evaluation test is conducted with respect to the braking operation of the vehicle.

With the aforementioned test apparatus, the brake pedal can be automatically depressed, and therefore the vehicle operator is able to conduct the evaluation test for the braking operation of the vehicle while driving the vehicle without operating the brake pedal. Furthermore, since a main portion of the test apparatus is fixedly set under the seat, the possibility of interfering with the vehicle operator when he/she enters or exits the vehicle or to perform smooth driving is reduced.

However, before conducting the evaluation test, the aforementioned test apparatus has to be installed in the vehicle by temporarily detaching the seat. After the test apparatus is installed in the vehicle, the seat is attached again such that the test can be started. Meanwhile, after the test is finished, the test apparatus is removed from the vehicle by temporarily detaching the seat. After the test apparatus is removed from the vehicle, the seat is attached again. Conducting the performance test, thus, requires much time and labor as aforementioned, preventing efficient and smooth testing.

The test apparatus is fixedly set under the seat, by which the direction for depressing the brake pedal by the control rod is defined. Accordingly, the direction for depressing the brake pedal cannot be adjusted. An axial tension of the control rod is detected by a load sensor attached to the control rod as a depressing load applied to the brake pedal. In the aforementioned test apparatus, the depressing load applied by the tip of the control rod to the brake pedal cannot be detected accurately, requiring further improvement in the accuracy of the evaluation test.

SUMMARY OF THE INVENTION

It is one object of the invention to provide a performance evaluation test method for automatically applying pressure to a control member using the seat efficiently without requiring detaching/attaching the seat.

According to one aspect of the invention, there is provided a method for conducting a vehicle performance evaluation test by automatically depressing a control member of the vehicle to be depressed by a vehicle operator using an actuator of a vehicle performance evaluation test apparatus. The method includes the steps of providing the actuator having a first end and a second end for pressing the control member, fixing the first end of the actuator to a seat of the vehicle, engaging the second end of the actuator with the control member of the vehicle, and causing the actuator to exert a depressing force to depress the control member relative to the seat so as to automatically depress the control member. Another aspect of the invention relates to a vehicle performance evaluation test apparatus which includes an actuator that is provided with a first end fixed to a seat of the vehicle and a second end engaging with the control member. The actuator automatically presses a control member of the vehicle to be depressed by an operator of the vehicle, and is operable to generate a force to depress the control member relative to the seat of the vehicle. The actuator further includes a rod member movable in a longitudinal direction of the vehicle so as to depress the control member.

One end of the actuator is fixed to the seat and the other end is engaged with the control member. The actuator generates the force for relatively pressing the control member with respect to the seat to automatically press the control member. As a result, the evaluation test for the vehicle performance can be performed requiring no need for removing or installing the seat.

According to one aspect of the invention, a direction of depressing a force receiving surface of the control member is adjusted to a predetermined direction by the actuator prior to automatic operation of the control member by the actuator. The actuator is adjusted such that the pressing direction with respect to a force receiving surface of the control member is aligned with a predetermined direction prior to automatic application of the depressing force to the control member by the actuator. Therefore, the evaluation test for the vehicle performance can be started in the state where the pressing direction with respect to the force receiving surface of the control member is accurately aligned with the predetermined direction.

According to one aspect of the invention, a depressing load applied to the force receiving surface of the control member by the second end of the actuator is detected, and the depressing operation is controlled on the basis of the detected depressing load. The depressing load applied to the force receiving surface of the control member from the end of the actuator is detected, and the pressing by the actuator is controlled based on the detected depressing load. Therefore the evaluation test for the vehicle performance can be properly performed by accurately controlling the depressing force applied to the control member from the end of the actuator.

According to one aspect of the invention, the depressing force applied to the control member is reduced by generating a force for driving the second end of the actuator in a direction reverse to the direction of the depressing force. The actuator is capable of generating a force for driving the end thereof in the pressing direction and in the reverse direction. The actuator generates the force to drive the end thereof in the direction reverse to the pressing direction such that the depressing force applied to the control member is reduced. This makes it possible to increase or decrease the depressing force applied to the control member with high response, thus reducing overshoot upon increase in the depressing force of the actuator to a target value or fluctuation caused by maintaining the depressing force at the target value compared with the conventional test method or apparatus that allows the depressing force to be increased or decreased only in the pressing direction. Accordingly the depressing force applied to the control member can be reduced or eliminated efficiently upon completion of the test.

According to one aspect of the invention, a state in which the first end of the actuator is fixed to the seat is adjusted by the vehicle operator who is seated on the seat prior to automatic depression of the control member. The fixed condition of the end of the actuator with respect to the seat can be adjusted by the vehicle operator already seated on the seat before automatically pressing the control member by the actuator. Therefore, even if the fixed condition of the end of the actuator with respect to the seat is affected when the vehicle operator is seated on the seat, the fixed condition of the end of the actuator can be adjusted such that it is surely fixed in accordance with the predetermined fixed condition with respect to the seat, and thereby the evaluation test for the vehicle performance can be conducted with the one end of the actuator surely fixed in accordance with the predetermined fixed condition.

According to one aspect of the invention, the actuator is able to adjust a direction of depressing a force receiving surface of the control member to be pressed prior to automatic operation of the control member by the actuator. The actuator is allowed to adjust the pressing direction with respect to the force receiving surface of the control member. Therefore, the actuator is adjusted to align the direction of the depressing force applied to the force receiving surface of the control member with the predetermined direction. This makes it possible to start the test in the state where the pressing direction to the force receiving surface of the control member is aligned with the predetermined direction.

According to one aspect of the invention, there is provided a load detector disposed at the second end of the actuator and operable to detect a depressing load applied to the force receiving surface of the control member by the second end of the actuator. The actuator is provided with the load detector at its end so as to detect the depressing load applied to the force receiving surface of the control member from the end of the actuator. Therefore, the evaluation test for the vehicle performance can be properly performed by accurately controlling the depressing force to be applied to the control member from the end of the actuator.

According to one aspect of the invention, the actuator is capable of generating a force to drive the second end in a direction in which the control member is depressed and in a direction reverse thereto. The actuator is capable of generating a force for driving its end in the pressing direction and in the reverse direction. The actuator generates the force to drive the end thereof in the direction reverse to the pressing direction such that depressing force applied to the control member is reduced. This makes it possible to increase or decrease the depressing force applied to the control member with good response. Unlike the conventional test method or apparatus that allows the depressing force of the actuator to be increased or decreased only in the pressing direction, overshoot upon increase in the depressing force of the actuator to a target value or fluctuation caused by maintaining the depressing force at the target value may be reduced. Accordingly the depressing force applied to the control member can be reduced or eliminated efficiently upon completion of the test.

According to one aspect of the invention, there is provided an adjustment that adjusts a state in which the first end of the actuator is fixed to the seat and is operable by the vehicle operator who is seated on the seat. There is provided the adjustment for adjusting the fixed condition of one end of the actuator with respect to the seat, which can be operated by the operator seated on the seat. Therefore, even if the fixed condition of the end of the actuator with respect to the seat is affected when the vehicle operator is seated on the seat, the fixed condition of the end of the actuator can be adjusted such that it is surely fixed in accordance with the predetermined fixed condition with respect to the seat, and thereby the evaluation test for the vehicle performance can be performed with the one end of the actuator surely fixed in accordance with the predetermined fixed condition.

According to one aspect of the invention, there is provided an attachment mounted on the second end of the actuator to be fixed to the control member. The attachment is operable to disconnect the second end of the actuator from the control member when a force equal to or greater than a predetermined value is exerted between the control member and the second end of the actuator in a direction such that the control member moves apart from the second end of the actuator.

The actuator is provided with the attachment at its end. When the force equal to or greater than a predetermined value is exerted between the control member and the actuator in the direction moving apart from each other, the end of the actuator is disengaged from the control member. Therefore, the vehicle operator is allowed to operate the control member by applying a strong force to the control member so as to be disconnected from the actuator when the vehicle operator finds it necessary to pressurize the control member even in the middle of the evaluation test.

According to one aspect of the invention, there is provided a releasable coupling that disconnects the first end of the actuator from the seat and disengages the second end of the actuator from the control member. The releasable coupling is operable by the vehicle operator who is seated on the seat. The releasable coupling serves to disconnect the end of the actuator from the seat, and to disengage the other end of the actuator from the control member. The vehicle operator is allowed to operate the releasable coupling while being seated on the seat. Therefore the possibility for the actuator to hinder the vehicle operator from smoothly getting off the vehicle can be decreased. The actuator, thus, can be easily removed upon completion of the evaluation test.

According to one aspect of the invention, the control member takes a form of a braking control member. Therefore, the evaluation test can be automatically conducted by automatically depressing the braking control member using the actuator.

Preferably, a length of the actuator is adjustable when in a non-operational state, and the actuator is adjusted to align a direction of depressing the force receiving surface of the control member with a predetermined direction of a position of the seat as viewed in a longitudinal direction of the vehicle.

Preferably, a depressing operation of the actuator is controlled on the basis of a deviation between a target depressing load and the detected depressing load.

Preferably, deceleration of the vehicle is detected, and a depressing operation of the actuator is controlled on the basis of a deviation between a target deceleration and the detected deceleration.

Preferably, the actuator takes the form of a depressing force generator having a first end and a second end, a seat-side attachment that fixes the first end of the depressing force generator to the seat of the vehicle, and a control-member-side attachment that fixes the second end of the depressing force generator to the control member.

The actuator may be provided with a coupling that detachably couples the depressing force generator with the seat-side attachment.

Preferably, the depressing force generator takes the form of a cylinder having a piston, a first chamber and a second chamber defined by the piston, and a pressure within at least one of the first and the second chambers is controlled. A pressure within the other chamber of the cylinder may be controlled to a constant pressure that is higher than an atmospheric pressure.

The cylinder may take the form of a pneumatic cylinder.

The first chamber and the second chamber of the cylinder may be allowed to be open to an ambient air when the vehicle performance evaluation test apparatus is in a non-operational state.

The seat-side attachment may include a seat engaging member having a horizontal portion that is placed on a seat body of the seat and a vertical portion that abuts on a front end of the seat body.

The seat side attachment may include a lower engaging member that engages with a lower surface of the seat body of the seat so that one end of the depressing force generator is fixed to the seat by holding the seat body between the horizontal portion of the seat engaging member and the lower engaging member while the vertical portion of the seat engaging member abuts on the front end of the seat body.

The seat-side attachment may further include a clamp load adjustment that adjusts a clamp load applied to the seat body. The seat-side attachment is operable by the vehicle operator who is seated on the seat.

The depressing force generator may have a spherical portion formed on the second end to be connected to the control member. The control-member-side attachment may include a socket that receives the spherical portion, and a mounting member that mounts the socket to the control member so that the depressing force is transmitted from the socket to the control member.

The mounting member may include an abutting member that abuts on a force receiving surface of the control member to be pressed such that a load detector is compressed between the abutting member and the socket member.

The control-member-side attachment may include a base member that supports the socket such that the depressing force is allowed to be transmitted from the socket to the control member, and a holding plate that is fixed to the base member and prevents the spherical portion from coming off the socket.

The holding plate may deform when a force equal to or greater than a predetermined value is exerted in a direction in which the spherical portion comes off the socket so as to allow the spherical portion to come off the socket.

BRIEF DESCRIPTION OF THE DRAWINGS

The invention will be described with reference to the following drawings in which like numerals refer to like elements and wherein.

DETAILED DESCRIPTION OF PREFERRED EMBODIMENTS

A preferred embodiment of the invention will be described in detail with reference to attached the drawings.

Figure 1:
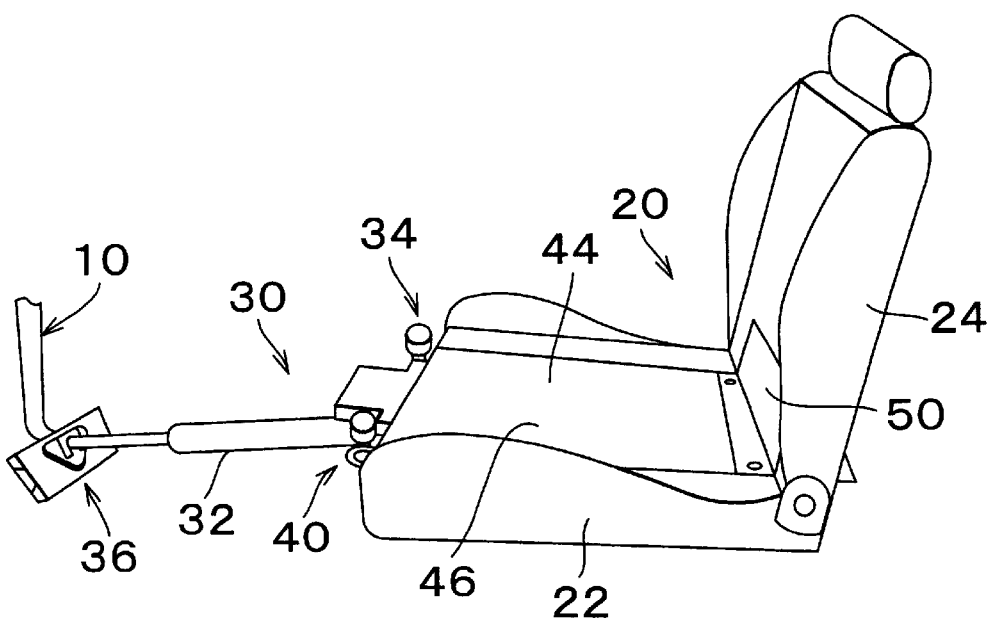
FIG. 1 is a perspective view of an actuator of a vehicle performance evaluation test apparatus according to an embodiment of the invention when it is attached to the seat of the vehicle.
Figure 2:
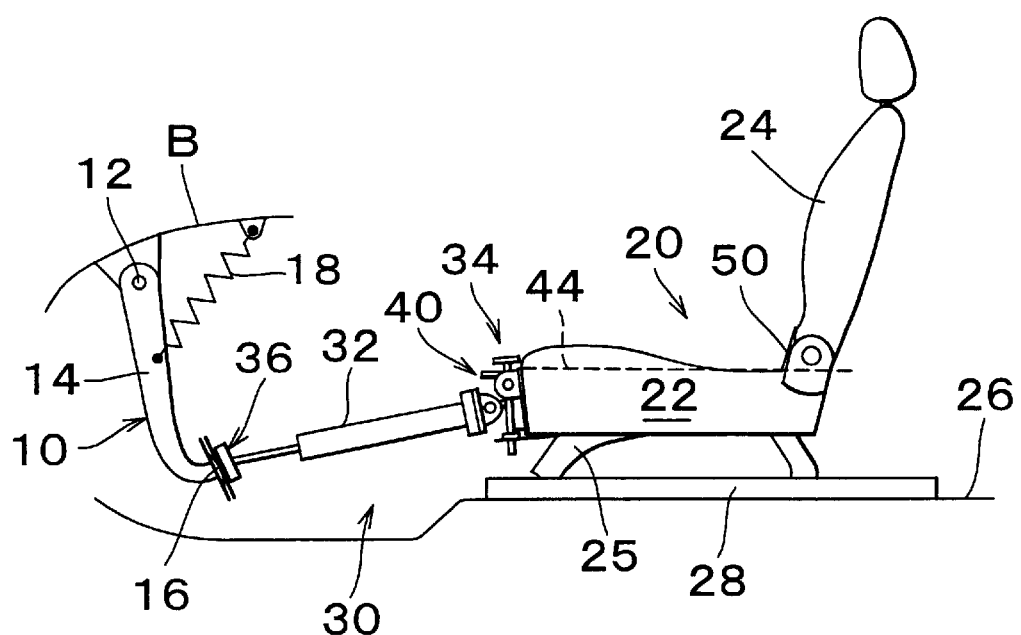
FIG. 2 is a side view of the actuator as shown in FIG. 1.
Figure 3:
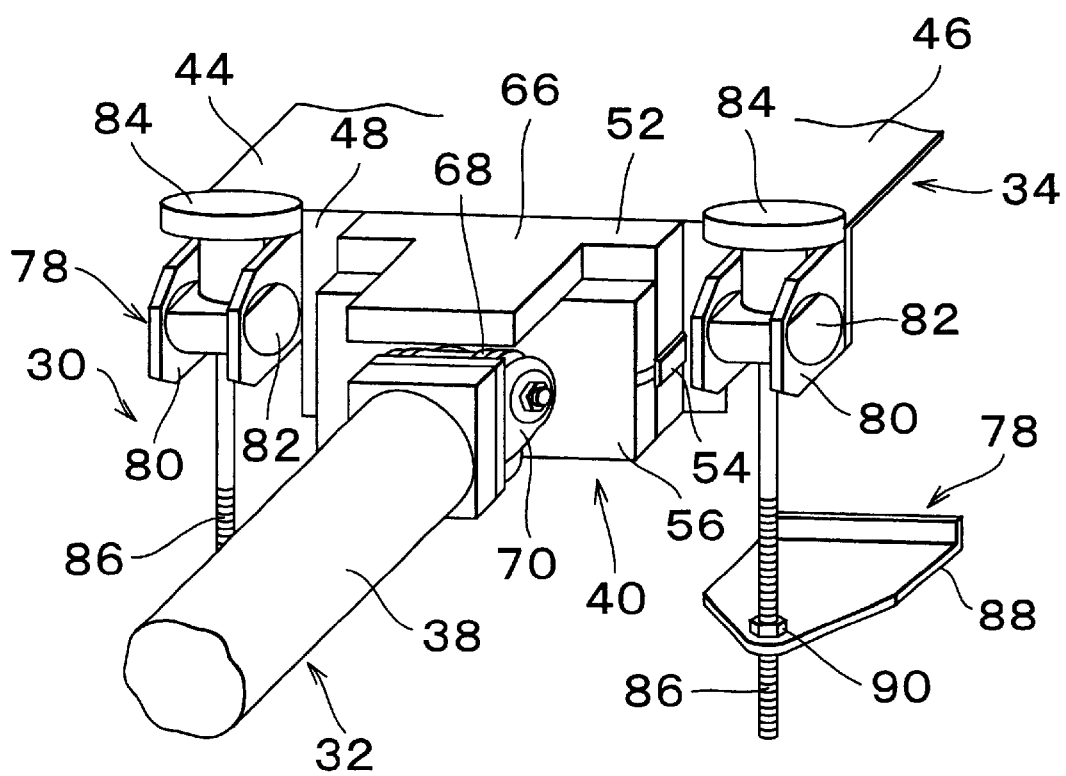
FIG. 3 is a perspective view showing a seat-side attachment of the actuator and a coupling in a coupled state.
Figure 4:
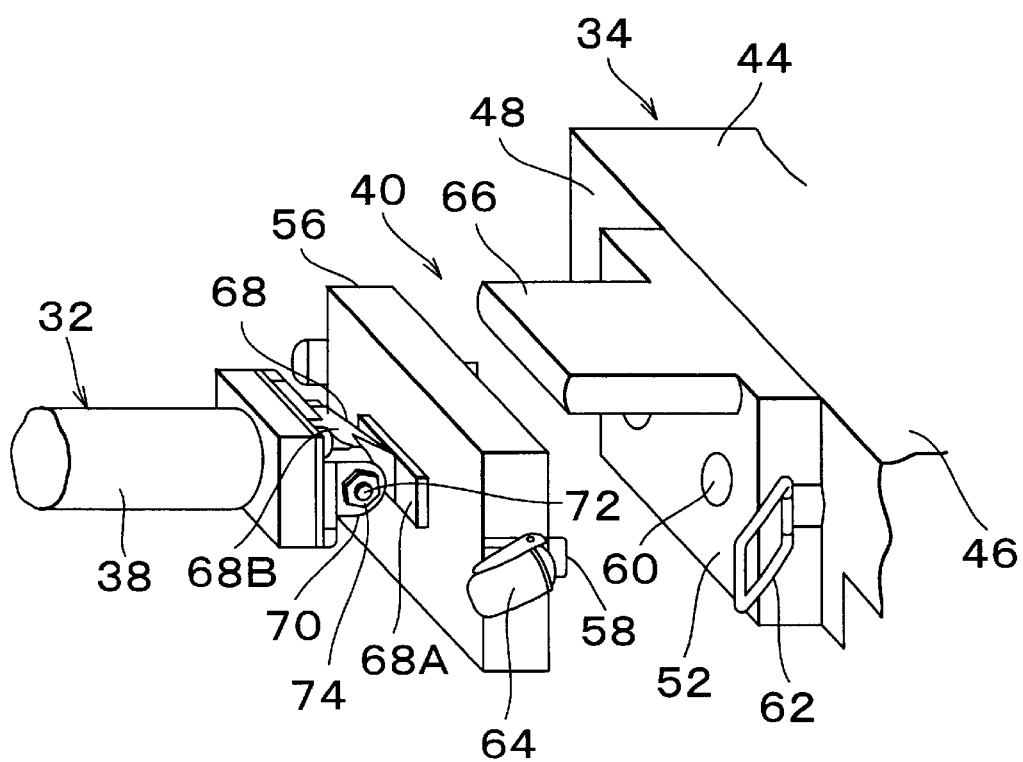
FIG. 4 is a perspective view of the coupling of the actuator in a separated state.
Figure 5:
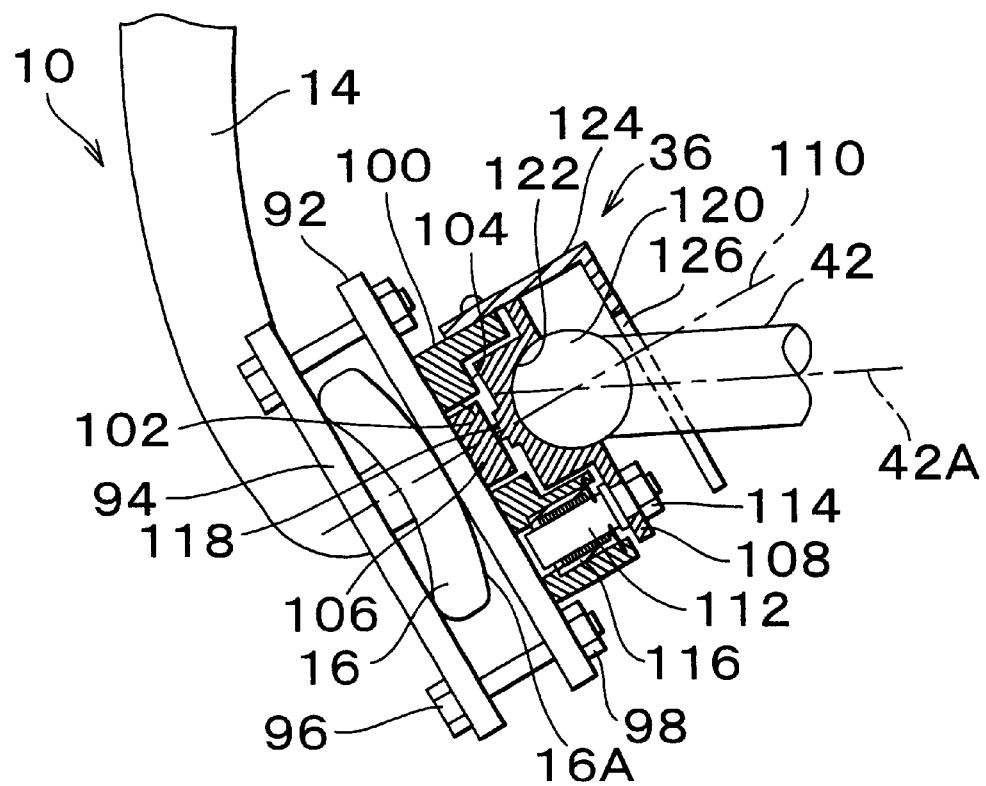
FIG. 5 is a sectional view of a pedal-side attachment of the actuator.
Figure 6:
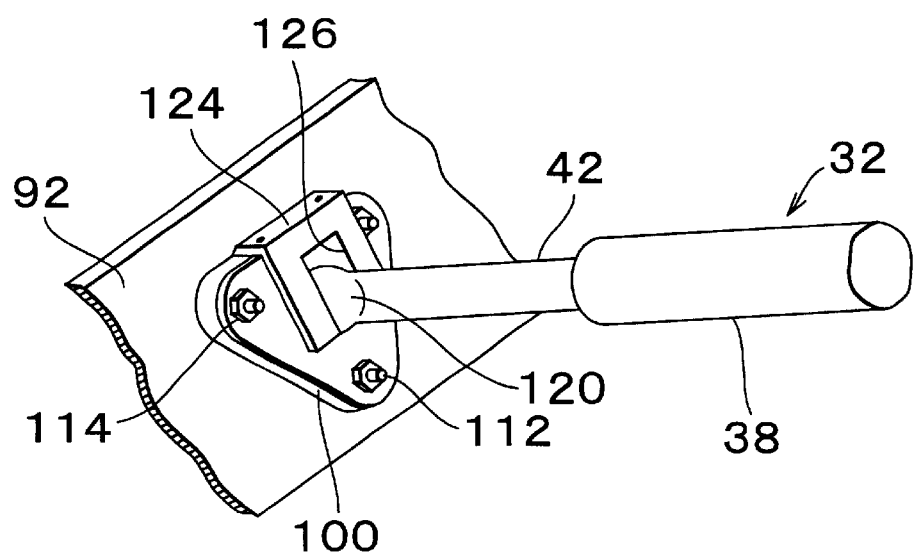
FIG. 6 is a perspective view of a main portion of the pedal-side attachment of the actuator.
Figure 7:
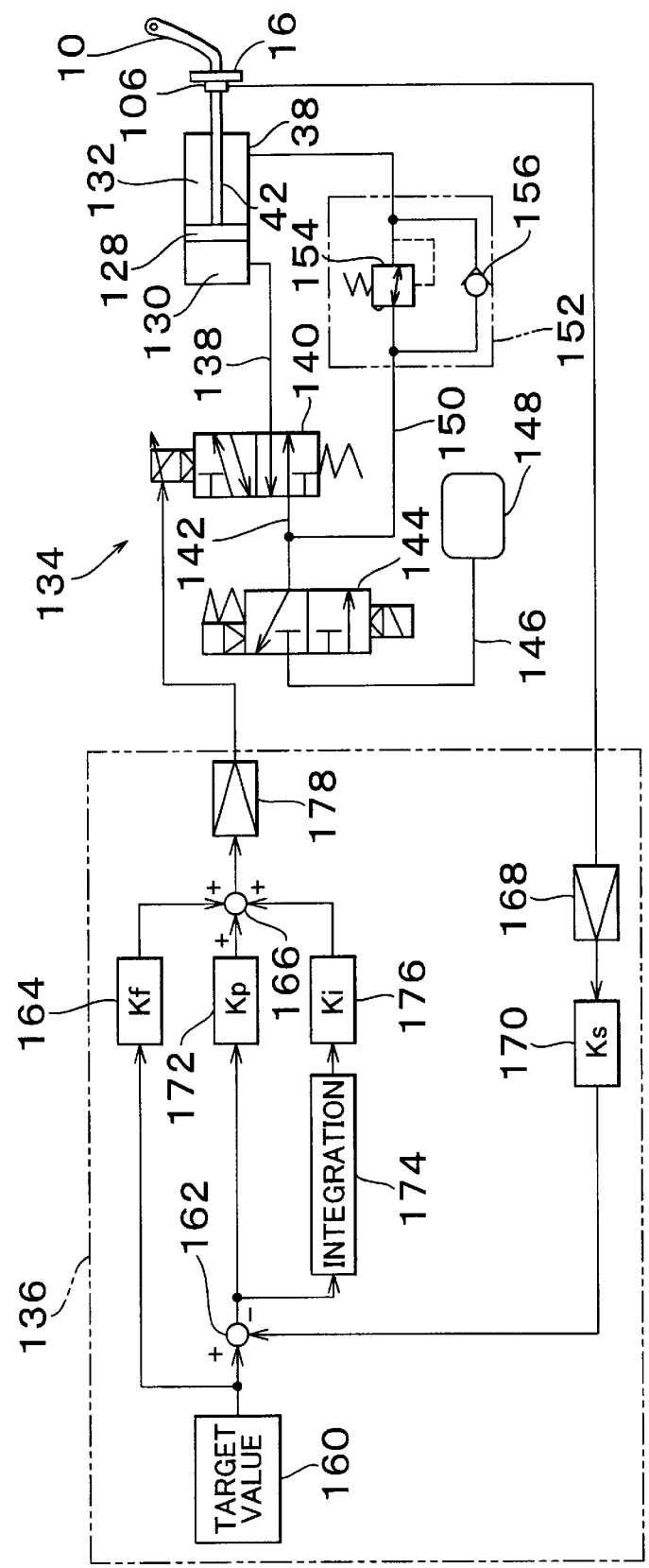
FIG. 7 is a diagram showing a pneumatic circuit and an electronic control unit for driving a pneumatic cylinder/piston device.

FIG. 1 is a perspective view of a pressing device (an actuator) of a vehicle performance evaluation test apparatus according to the preferred embodiment of the invention when the apparatus is installed on a vehicle. FIG. 2 is a side view of the pressing device as shown in FIG. 1. FIG. 3 is a perspective view showing a seat-side fixing device (attachment) of the pressing device and a connecting device in a connected state. FIG. 4 is a perspective view of the connecting device of the pressing device in a separated state. FIG. 5 is a section view of a pedal-side fixing device (attachment) of the pressing device. FIG. 6 is a perspective view of a main portion of the pedal-side fixing device of the pressing device. FIG. 7 is a diagram showing a pneumatic circuit and an electronic control unit for driving a pneumatic cylinder/piston device.

In these figures, a brake pedal 10 serving as a control member is operated by a vehicle operator (not shown). Generally the brake pedal 10 is provided with an arm 14 supported by a vehicle body B via a pivot pin 12 at an upper end thereof such that the arm 14 can pivotally move in a longitudinal direction of the vehicle, and a laterally extending pedal portion 16 integrally fixed at a lower end of the arm 14. The brake pedal 10 is pivotally biased to a normal position by a return spring 18 disposed between the arm 14 and the vehicle body B.

Referring to the drawings, a seat 20 on which the vehicle operator is seated includes a seat body 22 and a seat back 24 pivotally supported at a rear end of the seat body 22 by a lower end thereof, and a plurality of legs 25 are fixed to the seat body 22. Each leg 25 engages with a seat rail 28 such that the leg 25 is allowed to move in the longitudinal direction of the vehicle and is fixed thereon by a stopper (not shown). The rails are mounted to the floor 26 of the vehicle.

One end of a pressing device 30 is fixed at the seat 20 and the other end of the pressing device 30 is engaged with the pedal portion 16 of the brake pedal 10. The pressing device 30 includes a pneumatic cylinder/piston device 32 which is disposed in the longitudinal direction of the vehicle and serves as a pressing force generating device (generator), a seat-side fixing device 34, and a pedal-side fixing device 36. A cylinder 38 of the pneumatic cylinder/piston device 32 is detachably connected to the seat-side fixing device 34 through a connecting device 40. The pedal-side fixing device 36 is attached at a tip of a piston rod 42 of the pneumatic cylinder/piston device 32.

The seat-side fixing device 34 is provided with a seat engaging plate 44 having an L-like shape cross section. The seat engaging plate 44 includes a horizontal portion 46 to be located above the seat body 22 and a vertical portion 48 which abuts on a front end face of the seat body 22. A seat back abutting plate 50 is fixed to the horizontal portion 46 by welding or the like. A part of the horizontal portion 46 to the rear of the seat back abutting plate 50 is inserted between the seat body 22 and the seat back 24.

In the embodiment, the seat back abutting plate 50 is fixed to the horizontal portion 46 such that the vertical portion 48 abuts on the front end face of the seat body 22 when the rear part of the horizontal portion 46 is inserted between the seat body 22 and the seat back 24 until the seat back abutting plate 50 abuts on the seat back 24. The seat back abutting plate 50 may be attached to the horizontal portion 46 using, for example, a combination of a slot and a bolt so that the position of the seat back abutting plate 50 can be longitudinally adjusted.

As shown in FIGS. 3 and 4, a connecting device 40 is provided with a connecting board 52 fixed at a center part of the vertical portion 48 of the seat engaging plate 44 by welding or the like, and a board 56 to be detachably fixed to the connecting board 52 using a pair of hook assemblies 54. In this embodiment, the board 56 includes a pair of pins 58 and is positioned with respect to the connecting board 52 by fitting the pins 58 into corresponding pin holes 60 formed in the connecting board 52.

The hook assembly 54 includes a hook ring 62 pivotally attached at a side face of the connecting board 52 and a hook lever 64 pivotally attached at a side of the board 56. The board 56 is fixed to the connecting board 52 by pivotally moving the hook assembly 54 forward in a state where the hook lever 64 is engaged with the hook ring 62. Additionally a horizontally longitudinally extending blocking portion 66 is integrally provided at an upper edge of the connecting board 52. The blocking portion 66 prevents the pneumatic cylinder/piston device 32 and a part of the connecting device 40 from moving up to hit the vehicle operator sitting on the seat when the vehicle operator disengages the connecting device 40 by operating the hook assembly 54.

A flange portion 68A of a pivotal support member 68 is welded to a surface of the board 56 opposite to the surface of the board 56 having the pin 58. The pivotal support member 68 includes a tubular portion 68B which extends in the lateral direction of the vehicle and is disposed between a pair of brackets 70 fixed at one end of a cylinder 38 of the pneumatic cylinder/piston device 32. The tubular portion 68B is connected to the bracket 70 by a bolt 72 and a nut 74 inserted through those members. The pneumatic cylinder/piston device 32 is supported around an axis defined by the bolt 72 so as to move pivotally with respect to the connected board 56 in a vertical direction.

A pair of fixed condition adjustment assemblies 78 are provided on both sides of the connecting device 40 in the lateral direction of the vehicle. Each fixed condition adjustment assembly 78 includes a bracket 80 welded on the vertical portion 48 of the seat engaging plate 44. A pivot shaft 82 extending in the lateral direction is rotatably supported to the bracket 80. A vertically extending bolt 86 having a knob 84 at its upper end is inserted through the pivot shaft 82. The bolt 86 is supported by the pivot shaft 82 so as not to rotate relative to the pivot shaft 82.

The bolt 86 extends through a front end portion of an engaging plate 88 which engages with a bottom surface of the seat body 22, and is screwed on a nut 90 welded to the front end portion of the engaging plate 88. When the bolt 86 is turned by turning the knob 84, the engaging plate 88 accordingly moves up or down depending on the turning direction of the bolt 86. Accordingly, the seat body 22 is interposed between the seat engaging plate 44 and the engaging plate 88, and a compression load can be applied to the seat body 22.

As shown in FIGS. 5 and 6, the pedal-side fixing device 36 includes a pedal abutting plate 92 which abuts on a pedal surface 16A of a pedal portion 16 of the brake pedal 10, and a pair of pedal engaging plates 94 which engage with the pedal portion 16 on both sides of the arm 14 in the lateral direction of the vehicle. The pedal abutting plate 92 and the pedal engaging plates 94 are detachably fixed to the pedal portion 16 by bolts 96 inserted therethrough and nuts 98 screwed thereon. Further, the pedal abutting plate 92 is brought into abutment on a position P of the pedal surface 16A of the pedal portion 16, which is identical to the position of a shoe sole of the vehicle operator during normal braking operation when all pairs of the bolts 96 and the nuts 98 are tightened with substantially the same amount of force.

A base member 100 substantially formed in a triangular shape is welded to the surface opposite to the surface that faces the pedal engaging plate 92. At a center of the base member 100, an opening 102 and an opening 104 communicated therewith form a concave portion (hereinafter referred to as a concave portion 104). In the opening 102, a load sensor 106 is disposed with some play and fixed to the pedal abutting plate 92 by means of adhesion or the like. In the concave portion 104, a socket member 108 is provided so as to be reciprocable along an axis 110 which is perpendicular to the surface of the pedal abutting plate 92.

Flange portions of the socket member 108 are fixed with three guide pins 112 are nuts 114. The guide pins 112 are located on a circumference of the axis 110 therealong at equal intervals. The base member 100 is provided with three ball bearing units 116 for guiding corresponding guide pins 112 in the direction parallel with the axis 110. The socket member 108 is provided with a pressing member 118 which protrudes toward the load sensor 106 along the axis 110 and a hemispherical hollow portion 122 for rotatably receiving a spherical portion 120 provided at the tip of the piston rod 42 in an opposite side thereof to which the pressing member 118 is provided. A center O of the hollow portion 122 is located on the axis 110, and therefore an axis 42A which is an axis of the piston rod 42 and the axis 110 cross at the center O.

In such a construction, the depressing force generated by the pneumatic cylinder/piston device 32 is transmitted to the socket member 108 via the spherical portion 120. However, the depression force acting in the direction along the axis 110 is only transmitted to the pedal portion 16 of the brake pedal 10 via the pressing member 118, the load sensor 106, and the pedal abutting plate 92. Therefore the load sensor 106 is capable of detecting only the depression force applied to the pedal surface 16A of the pedal portion 16 in the direction along the axis 110 accurately.

Furthermore, fixed at a side face of the base member 100 is a holding plate 124 having an L-like cross section so as to prevent the spherical portion 120 from coming off the hollow portion 122. The holding plate 124 includes a substantially rectangular cut-out 126 for receiving the piston rod 42. The cut-out 126 abuts on or overhangs close to the spherical portion 120. The holding plate 124 is formed from a metal plate such as a steel plate. When a force greater than a predetermined value is applied to the spherical portion 120 in a direction where the spherical portion 120 comes off the hollow portion 122, the spherical portion 120 elastically or plastically deforms the holding plate 124 in a direction so that the holding plate 124 moves away from the base member 100. As a result, the spherical portion 120 moves away from the socket member 108 such that the piston rod 42 is disconnected from the pedal portion 16.

As schematically shown in FIG. 7, the pneumatic cylinder/piston device 32 includes a first chamber 130 and a second chamber 132 both defined by a piston 128 fixed to the piston rod 42. A pressure P1 within the first chamber 130 and a pressure P2 within the second chamber 132 are controlled by a pneumatic circuit 134 and an electronic control unit 136 for increasing or decreasing the depressing force applied from the pressing device 30 to the pedal portion 16 of the brake pedal 10.

The first chamber 130 of the pneumatic cylinder/piston device 32 is connected to a first port of an electropneumatic proportional valve 140 via a pipe 138. A second port of the electropneumatic proportional valve 140 is connected to one end of a pipe 142. A first port of a master valve 144 is connected to the other end of the pipe 142. A second port of the master valve 144 is connected to an air tank 148 via a pipe 146. A pressure in the air tank 148 is controlled to a value between predetermined upper and lower limit values using an air pump or the like.

One end of a pipe 150 is connected to the pipe 142 and the other end of the pipe 150 is connected to the second chamber 132 of the pneumatic cylinder/piston device 32. Provided midway in the pipe 150 is a regulating device 152 provided with a regulator 154 for controlling a pressure at the cylinder piston device 32 side as a pilot pressure, and a check valve 156 that allows the compressed air to flow from the second chamber 132 to the pipe 142 by bypassing the regulator 154. The regulator 154 and the check valve 156 cooperate with each other to control the pressure P2 within the second chamber 132 to a substantially constant value.

When the vehicle performance evaluation test apparatus is not operated, that is, when no control signal is sent to a solenoid of the master valve 144 from the electronic control unit 136, a valve position of the master valve 144 is set at a first position as shown in FIG. 7. As a result, communication between the pipes 146 and 142 is disconnected, and the pipe 142 is opened to an ambient air. Conversely, when the control voltage is applied to the solenoid of the master valve 144 by the electronic control unit 136, the valve position of the master valve 144 is switched to a second position. As a result, communication between the pipes 146 and 142 is made.

On the other hand, when the vehicle performance evaluation test apparatus is not operated, that is, when no control signal is sent to a solenoid of the electropneumatic proportional valve 140 by the electronic control unit 136, the position of the electropneumatic proportional valve 140 is set at the first position as shown in FIG. 7. Then the first chamber 130 is opened to the ambient air via the pipe 138. Conversely, when the control voltage is applied to the solenoid of the electropneumatic proportional valve 140 by the electronic control unit 136, the valve position is switched to a second position. As a result, communication between the pipes 142 and 138 is made. A compressed air at a pressure in proportion to the applied control voltage is then supplied into the first chamber 130 of the pneumatic cylinder/piston device 32 via the pipe 138. Accordingly, the pressure P1 of the first chamber 130 is controlled to be increased or decreased.

Accordingly when the vehicle performance evaluation test apparatus is not operated, the pressure P1 in the first chamber 130 and the pressure P2 in the second chamber 132 of the pneumatic cylinder/piston device 32 become ambient air pressures. Therefore a position of the piston 128 with respect to the cylinder 38 of the pneumatic cylinder/piston device 32 can be freely changed. This makes it possible to freely adjust the length of the pneumatic cylinder/piston device 32.

The electronic control unit 136 includes a target value setting unit 160 for setting a target value, for example, a target pedal depressing force Fbpt applied to the pedal portion 16 of the brake pedal 10 by the operator. An output value of the target value setting unit 160, that is, a signal indicating the target value, for example, the target pedal depressing force Fbpt is concurrently input to a positive terminal of an adder 162 and a gain multiplier 164 for a feed-forward control, and then is input to an adder 166 after calculation of a feed-forward gain Kf performed by the multiplier 164.

An output of the load sensor 106 installed in the pedal side fixing device 36, that is, the signal indicating the pedal depressing force Fbp applied to the pedal portion 16 of the brake pedal 10 by the pressing device 30, is sent to the gain multiplier 170 via an amplifier 168. After a gain Ks is applied through multiplication by the gain multiplier 170, the signal is input to a negative terminal of the adder 162. An output of the adder 162 is then input to a proportional gain multiplier 172 for feedback control. After a proportional gain Kp is applied through multiplication by the proportional gain multiplier 172, the signal is input to the adder 166.

An output value of the adder 162 also is sent to an integration circuit 174, and an output of the integration circuit 174 is sent to an integral gain multiplier 176 for feedback control. After an integral gain Ki is applied through a multiplication by the integral gain multiplier 176, the signal is sent to the adder 166. An output of the adder 166 is sent to the solenoid of the electropneumatic proportional valve 140 via the amplifier 178 as a control command signal for controlling the electropneumatic proportional valve 140 to thereby control the pressure P1 within the first chamber 130 of the pneumatic cylinder/piston device 32 to be increased or decreased.

The electronic control unit 136 may be formed as a control device such as the one constituted of a drive circuit and a general type of a computer which includes a CPU, a ROM, a RAM and input/output ports, all connected to one another via a bidirectional common bus. A calculation by the adder 162 and the like may be performed by a control program installed in the micro computer.

When a braking performance of the vehicle is tested for evaluation using the aforementioned vehicle performance evaluation test apparatus, the rear end of the horizontal portion 46 of the seat engaging plate 44 of the seat-side fixing device 34 is inserted between the seat body 22 of the seat 20 and the seat back 24, and the seat engaging plate 44 is positioned with respect to the seat 20 such that the seat back abutting plate 50 abuts on the seat back 24 and the vertical portion 48 abuts on a front face of the seat body 22.

Then, the engaging plate 88 of the fixed condition adjustment assembly 78 is positioned underneath the seat body 22. When the knob 84 is turned in the aforementioned state, the seat body 22 is interposed under pressure between the horizontal portion 46 of the seat engaging plate 44 and the engaging plate 88 to thereby fix the seat-side fixing device 34 to the seat 20. Then the board 56 is connected to the connecting board 52 via the hooking assembly 54, fitting the pins 58 of the connecting device 40 into the pin holes 60. In such a manner, one end of the pneumatic cylinder/piston device 32 is fixed to the seat 20 via the connecting device 40 and the seat-side fixing device 34.

Next, the other end of the pneumatic cylinder-piston device 32 is fixed to the pedal portion 16 of the brake pedal 10 by interposing the pedal portion 16 of the brake pedal 10 under pressure between the pedal abutting plate 92 and the engaging plates 94 of the pedal-side fixing device 36, and screwing the nuts 98 on the bolts 96. Then the stopper of the seat 20 is released such that the seat 20 is moved in the longitudinal direction of the vehicle. The angle of the pneumatic cylinder/piston device 32 is then adjusted with respect to the pedal surface 16A of the pedal 16, and the seat 20 is fixed by the stopper. As pressures in the first chamber 130 and the second chamber 132 of the pneumatic cylinder/piston device 32 are both equal to the ambient pressure, the length of the pneumatic cylinder/piston device 32 freely changes as the seat 20 moves in the longitudinal direction.

The vehicle operator is seated on the seat 20 and turns the knob 84 of the fixed condition adjustment device 78 to adjust a squeezing load applied to the seat body 22 between the horizontal portion 46 of the seat engaging plate 44 and the engaging plate 88 such that the seat-side fixing device 34 is securely fixed to the seat 20. After completing the preparation for the evaluation test, the operator starts the evaluation test by operating, for example, the feed-forward gain automatic setting switch of the electronic control unit 136 and the like.

For example, for the test of evaluating a braking performance of the vehicle with respect to a braking distance, the valve position of the master valve 144, the main switch (not shown) is turned off in a state where the vehicle is stopped. Upon switching of the master valve 144 from the first position to the second position, the test apparatus is started. A target depressing force Fbpt to be applied to the brake pedal 10 is set by the target value setting unit 160. Then the feed-forward gain Kf is calculated through multiplication by the gain multiplier 164 such that the depressing force applied to the pedal portion 16 of the brake pedal 10 by the pressing device 30 becomes smaller than the target depressing force.

Next the depressing force is applied to the pedal portion 16 of the brake pedal 10 by the pressing device 30 in the state where the vehicle is running at a predetermined speed. The depressing force is initially increased in accordance with the feed-forward control amount based on a product Fbpt·Kf of the target depressing force Fbpt and the feed-forward gain Kf Then a deviation ΔFbp between the target depressing force Fbpt and an actual depressing force Fbp detected by the load sensor 106 is calculated. The depressing force is then controlled according to the feed-forward control amount based on the product Fbpt·Kf and a feedback control amount based on a product ΔFbp·Kp of the deviation ΔFbp and the proportional gain Kp calculated by the gain multiplier 172.

Further, the depressing force is controlled in accordance with the feed-forward control amount based on the product Fbpt·Kf, the feedback control amount based on the product ΔFbp·Kp, and a feedback control amount based on a product ΔFbpi·Ki of an integral value ΔFbpi of the deviation ΔFbp of the depressing force and an integral gain Ki calculated by the gain multiplier 176. Accordingly the depressing force applied to the pedal portion 16 of the brake pedal 10 is accurately controlled. As a result, the braking distance, that is, the distance moved by the vehicle from start of the braking to stop of the vehicle may be measured.

For the test of evaluating the vehicle performance regarding a deceleration, a target deceleration is set by the target value setting unit 160. A deceleration Gxb is calculated based on a longitudinal acceleration of the vehicle detected by a longitudinal acceleration sensor (not shown). The pressing device 30 is then controlled based on the feed-forward control amount and the feedback control amount such that the deceleration Gxb of the vehicle conforms to the predetermined deceleration Gxbt. Controlling the depressing force to be applied to the pedal portion 16 of the brake pedal 10 from the pressing device 30 in such a manner, the vehicle performance regarding the deceleration is evaluated by determining whether or not the deceleration Gxb of the vehicle conforms to the targeted deceleration Gxbt.

As is described above, according to the embodiment shown in the figures, the pressing device 30 is connected to the seat body 22 of the seat 20 by a first end thereof via the seat-side fixing device 34, and to the pedal portion 16 of the brake pedal 10 by the other end thereof via the pedal-side fixing device 36, and the pressing force is applied to the pedal portion 16 of the brake pedal 10 relatively with respect to the seat 20. Therefore, the evaluation test for the braking performance of the vehicle can be performed without disassembling/assembling the seat 20, thus conducting the test for evaluating the braking performance of the vehicle easily and efficiently.

Further, according to the embodiment shown in the figures, one end of the pneumatic cylinder/piston device 32 is pivotally connected to the seat-side fixing device 34 via the connecting device 40. The pedal-side fixing device 36 serves to fixedly connect the piston rod 42 of the cylinder/piston device 32 pivotally movably with respect to the pedal portion 16. Therefore, an angle of the pneumatic cylinder/piston device 32 with respect to the pedal portion 16 can be adjusted to a predetermined angle by adjusting a position of the seat 20 in the longitudinal direction of the vehicle. In this case, as the length of the pneumatic cylinder/piston device 32 can be freely changed, the adjustment of the angle of the cylinder piston 32 with respect to the pedal portion 16 can be easily performed.

Further, according to the embodiment shown in the figures, the pedal-side fixing device 36, regardless of how the pneumatic cylinder/piston device 32 is oriented with respect to the pedal surface 16A of the pedal portion 16, is allowed to transmit the pressing force generated by the pneumatic cylinder/piston device 32 to the pedal portion 16 along the axis 110. The axis 110 is aligned with a direction in which the operator applies the depressing force to the pedal portion 16 using the pedal abutting plate 92. The load sensor 106 detects the pressing force applied from the tip of the pneumatic cylinder/piston device 32 to the pedal potion 16 along the axis 110. This makes it possible to detect the depressing force to the brake pedal 10 applied by the pressing device 30 more accurately compared with the case in which the axial force of the pneumatic cylinder/piston device 32 is detected as the depressing force. The evaluation test for the braking performance of the vehicle, thus, can be performed with high accuracy.

According to the embodiment shown in the figures, the pedal-side fixing device 36 connects the tip of the pneumatic cylinder/piston device 32 with the pedal portion 16 such that a force can be transmitted in the direction where the depressing force is applied to the pedal portion 16 and in the direction reverse thereto. The pneumatic cylinder/piston device 32 is allowed to generate the force both in the depressing direction and the direction reverse thereto by controlling a pressure P1 within a first chamber 130 while keeping a pressure P2 within a second chamber of the pneumatic cylinder/piston device 32 at a substantially constant pressure. This makes it possible to increase or decrease the depressing force applied to the brake pedal 10 with good response irrespective of the slide resistance of the pneumatic cylinder/piston device 32. As a result, an amount of a change in the depressing force, which is caused by overshooting at increasing the pressing force of the pressing device to a predetermined value or which arises while maintaining the pressing force at the predetermined value, can be decreased. Therefore the evaluation test for the braking performance can be performed highly accurately and, when the evaluation test for the braking performance has been completed, the pressing force applied to the brake pedal 10 can be decreased to be eliminated efficiently.

Further, according to the embodiment shown in the figures, the horizontal portion 46 of the seat engaging plate 44 of the seat-side fixing device 34 is located on the seat body 22 of the seat 20. As the vehicle operator is seated on the horizontal portion 46, the compression load applied to the seat body 22 by the horizontal portion 46 and the engaging plate 88 is decreased. However, the seat body 22 can be adequately compressed between the horizontal portion 46 and the engaging plate 88 through the operation of the fixed condition adjustment device 78 by the vehicle operator while sitting on the horizontal portion 46. Accordingly, the evaluation test can be performed in the state where one end of the pressing device 30 is firmly and securely fixed with the seat 20.

Further, according to the embodiment shown in the figures, when the pedal-side fixing device 36 receives a strong force greater than a predetermined value in the direction where the spherical portion 120 formed on a tip of the piston rod 42 to come off the hollow portion 122 of the socket member 108, the holding plate 124 elastically deforms or plastically deforms to disengage one end of the cylinder/piston device 32 and the pedal portion 16 of the brake pedal 10. Therefore the vehicle operator is allowed to stop the vehicle by forcefully depressing the pedal portion 16 to depress the brake pedal 10 even though an abnormality such as locking occurs in the pneumatic cylinder/piston device 32.

Preferably the holding plate 124 is made of a material that does not substantially plastically-deform but elastically deforms to disconnect one end of the pneumatic cylinder/piston device 32 and the pedal portion 16. In such a case, the ball or the spherical portion 120 can be fitted into the hollow portion 122 while elastically deforming an edge of the holding plate 124 in a direction away from the socket member 108. Therefore the evaluation test can be restarted without replacing the holding plate 124.

Further, according to the embodiment shown in the figures, one end of the pneumatic cylinder/piston device 32 is detachably connected to the seat-side fixing device 34 via the connecting device 40. Therefore, the seat-side fixing device 34 can be fixed to the seat body 22 and the other end of the pneumatic cylinder/piston device 34 can be engaged with the pedal portion 16 via the pedal-side fixing device 36 in the state where the one end of the pneumatic cylinder/piston device 34 is disconnected from the seat-side fixing device 34. On the other hand, it is also possible to remove the seat-side fixing device 34 from the seat body 22 or remove the pedal-side fixing device 36 from the pedal portion 16 after releasing the connection made at the connecting device 40 by operating the hooking assembly 54. Accordingly, attachment/detachment of the pressing device 30 may be easier compared with the case without the connecting device 40.

Further, according to the embodiment shown in the figures, the vehicle operator is allowed to disconnect one end of the pneumatic cylinder/piston device 32 from the seat-side fixing device 34 at the connecting device 40 by operating the hooking assembly 54 while being seated on the seat 20. Therefore, the vehicle operator is allowed to get off the vehicle upon completion of the test without being interfered with by, for example, the pressing device 30.

Further, according to the embodiment shown in the figures, the pressing device 30 is provided with the pneumatic cylinder/piston device 32. The first and second chambers of the pneumatic cylinder/piston device 32 can be opened to the ambient air momentarily upon switching of the valve positions of the electropneumatic proportional valve 140 and the master valve 144 from the second positions to the first positions. Hence the vehicle operator, if necessary, is allowed to suspend the test and operate the brake pedal 10 intentionally by applying strong depressing force to the pedal portion 16 without disconnecting one end of the pneumatic cylinder/piston device 32 from the pedal portion 16 at the pedal-side fixing device 36 by forcefully depressing the pedal portion 16.

Further, according to the embodiment shown in the figures, the rear end of the seat engaging plate 44 is inserted between the seat body 22 and the seat back 24, where the abutting plate 50 abuts on the seat back 24. Therefore, compared to a case where the horizontal portion 46 of the seat engaging plate 44 is simply placed on the seat body 22, the one end of the pressing device 30 can be securely fixed to the seat body 22 and also chances for the seat-side fixing device 34 to be moved upward due to the pressing force generated by the pneumatic cylinder/piston device 32 is effectively decreased.

The invention is not limited to the embodiment described above. It is obvious to a person skilled in the art to which the invention pertains that the invention can be embodied in various forms without departing from the invention.

For example, in the embodiment described above, the depressing force applied to the control member is generated by the pneumatic cylinder/piston device 32 of the pressing device 30. However, the depressing force can be generated by a hydraulic type cylinder/piston device, an electric device including a rotary drive device such as an electric motor and a rotary-linear motion converting mechanism, for example, a ball screw, or an electromagnetic device which electromagnetically generates the depressing force.

Further, in the embodiment described above, an orientation of the pressing device 30 with respect to the pedal surface 16A of the pedal portion 16 of the brake pedal 10 is adjusted by adjusting the length of the pneumatic cylinder/piston device 32 and the position of the seat 20 in the longitudinal direction of the vehicle. However, the orientation of the pressing device 30 with respect to the pedal surface 16A of the pedal portion 16 of the brake pedal 10 may be adjusted by adjusting a position of the seat-side end of the pneumatic cylinder/piston device 32 in a vertical direction.

Further in the embodiment described above, a pair of the fixed condition adjustment assemblies 78 are provided in both sides of the connecting device 40 towards the lateral direction of the vehicle. The fixed condition adjustment assemblies 78 are operated such that the fixed condition of the one end of the pressing device 30 with respect to the seat 20 is adjusted after the vehicle operator is seated on the seat 20. However, the fixed condition adjustment assemblies 78 may be omitted.

In the embodiment as described above, the pneumatic cylinder/piston device 32 is detachably connected to the seat-side fixing device 34 via the connecting device 40 and, where necessary, the connection can be released by the hooking assembly 54. However, the connecting device 40 or the hooking assembly 54 may be omitted. Further, a front end of the pneumatic cylinder/piston device 32 and the pedal portion 16 of the brake pedal 10 may be detachably connected such that, if necessary, they can be disconnected by the vehicle operator.

Further, in the embodiment described above, the load generated along the axis 110 by the pneumatic cylinder/piston device 32 is fully transmitted to the pedal portion 16 of the brake pedal 10 via the load sensor 106. However, the load generated along the axis 110 may be partially transmitted to the load sensor 106.

Further, in the embodiment described above, the method and the apparatus of the invention are applied to the evaluation test for the braking performance of the vehicle. However, the method and the apparatus may also be applied to the evaluation test for acceleration performance of the accelerator of the vehicle.

As described above in detail, it is not necessary to remove and reinstall the seat for conducting the evaluation test for the vehicle performance. Therefore the test can be conducted in an easier and more efficient manner than the test using the conventional vehicle performance evaluation test apparatus.

In the illustrated embodiment of the invention, the pressing device can be adjusted such that the pressing direction with respect to the force receiving surface of the control member conforms to the predetermined direction prior to automatic application of the pressure to the control member by the pressing device. Therefore the evaluation test for the vehicle performance can be in the state where the direction of the pressure applied to the force receiving surface of the control member is accurately set to the predetermined direction. Therefore the evaluation test for the vehicle performance can be performed more accurately compared with the test using the conventional vehicle performance evaluation test apparatus as described above.

Further in the illustrated embodiment of the invention, the pressing load applied to the force receiving surface of the control member from the other end of the pressing device is detected, and the pressing force applied from the other end of the pressing device to the control member is properly controlled. Therefore the evaluation test for the vehicle performance can be performed highly accurately compared to the conventional vehicle performance evaluation test apparatus described above which detects the axial force of the control rod.

In the illustrated embodiment of the invention, when the depressing force applied to the control member is required to be reduced, the driving force in the direction opposite to the depressing direction can be generated. The depressing force applied to the control member can be increased/decreased with better response compared with the conventional test apparatus in which the depressing force in the depressing direction is only increased/decreased. This makes it possible to reduce the overshooting upon increase in the depressing force of the pressing device to the target value and a fluctuation for keeping the depressing force at the target value. The evaluation test for the vehicle performance can be performed accurately, and the depressing force applied to the control member is efficiently and surely decreased to be removed upon completion of the evaluation test for the vehicle performance.

In the illustrated embodiment of the invention, the vehicle operator is allowed to be seated on the seat and then adjust the fixed condition of one end of the pressing device with respect to the seat before starting automatic operation of the control member using the pressing device. Even if the fixed condition of the end of the pressing device with respect to the seat is deteriorated when the vehicle operator is seated on the seat, the fixed condition can be adjusted to fix the end of the pressing device to the seat in a predetermined condition. Therefore the evaluation test for the vehicle performance can be conducted in the state where one end of the pressing device can be fixed to the seat in the predetermined condition.

In the illustrated embodiment of the invention, the vehicle operator is allowed to disconnect one end of the pressing device from the control member by operating the control member with a strong force when he/she feels it necessary to operate the control member by himself/herself even in the middle of the test. Therefore, the vehicle operator is capable of intentionally operating the control member in case of need.

In the illustrated embodiment of the invention, the vehicle operator is allowed to operate the releasing device so as to disconnect one end of the pressing device from the seat or disengage the other end of the pressing device from the control member. Therefore, chances for the pressing device to hinder the operator from smoothly getting off the vehicle can be reduced and also the pressing device can be easily removed upon completion of the evaluation test.

In the illustrated embodiment of the invention, the control member as the braking member can be automatically depressed, thus allowing the evaluation test for the vehicle performance to be automatically performed.

While the invention has been described with reference to preferred embodiments thereof, it is to be understood that the invention is not limited to the disclosed embodiments or constructions. On the contrary, the invention is intended to cover various modifications and equivalent arrangements. In addition, while the various elements of the disclosed invention are shown in various combinations and configurations, which are exemplary, other combinations and configurations, including more, less or only a single element, are also within the spirit and scope of the invention.

What is claimed is:

1. A method for conducting a vehicle performance evaluation test by automatically depressing a control member of the vehicle to be depressed by a vehicle operator using an actuator of a vehicle performance evaluation test apparatus, comprising:

providing an actuator for depressing the control member, the actuator having a first end and a second end;

fixing the first end of the actuator to a seat of the vehicle;

engaging the second end of the actuator with the control member of the vehicle; and causing the actuator to exert a depressing force to depress the control member relative to the seat so as to automatically depress the control member.

2. The method according to claim 1, wherein a direction of depressing a force receiving surface of the control member is adjusted to a predetermined direction by the actuator prior to automatic operation of the control member by the actuator.

3. The method according to claim 2, wherein a length of the actuator is adjustable when in a non-operational state, and wherein the actuator is adjusted to align the direction of depressing the force receiving surface of the control member with a predetermined direction of a position of the seat as viewed in a longitudinal direction of the vehicle.

4. The method according to claim 1, wherein a depressing load applied to a force receiving surface of the control member by the second end of the actuator is detected, and the depressing operation is controlled on the basis of the detected depressing load.

5. The method according to claim 4, wherein a depressing operation of the actuator is controlled on the basis of a deviation between a target depressing load and the detected depressing load.

6. The method according to claim 4, further comprising detecting a deceleration of the vehicle, and controlling a depressing operation of the actuator on the basis of a deviation between a target deceleration and the detected deceleration.

7. The method according to claim 1, wherein the depressing force applied to the control member is reduced by generating a force for driving the second end of the actuator in a direction reverse to the direction of the depressing force.

8. The method according to claim 1, wherein a state in which the first end of the actuator is fixed to the seat is adjusted by the vehicle operator who is seated on the seat prior to automatic depression of the control member.

9. A vehicle performance evaluation test apparatus, comprising:
an actuator that automatically presses a control member of the vehicle to be depressed by an operator of the vehicle, the actuator including a first end to be fixed to a seat of the vehicle and a second end engageable with the control member, the actuator being operable to generate a force to depress the control member relative to the seat of the vehicle;
wherein the actuator comprises a rod member movable in a longitudinal direction of the vehicle so as to depress the control member.

10. The apparatus according to claim 9, wherein the first end of the actuator is fixed to a front end of the seat of the vehicle.

11. The apparatus according to claim 9, wherein the actuator comprises a depressing force generator having a first end and a second end, a seat-side attachment that fixes the first end of the depressing force generator to the seat of the vehicle, and a control-member-side attachment that fixes the second end of the depressing force generator to the control member.

12. The apparatus according to claim 11, wherein the first end of the depressing force generator is fixed to a front end of the seat of the vehicle.

13. The apparatus according to claim 11, wherein the actuator further comprises a coupling that detachably couples the depressing force generator with the seat-side fixing device.

14. The apparatus according to claim 11, wherein the depressing force generator comprises a cylinder having a piston, a first chamber and a second chamber defined by the piston, wherein a pressure within at least one of the first and the second chambers is controlled.

15. The apparatus according to claim 14, wherein a pressure within the other chamber of the cylinder is controlled to a constant pressure that is higher than an atmospheric pressure.

16. The apparatus according to claim 14, wherein the cylinder comprises a pneumatic cylinder.

17. The apparatus according to claim 15, wherein the cylinder comprises a pneumatic cylinder.

18. The apparatus according to claim 15, wherein the first chamber and the second chamber of the cylinder are allowed to be open to an ambient air when the vehicle performance evaluation test apparatus is in a non-operational state.

19. The apparatus according to claim 11, wherein the seat-side attachment includes a seat engaging member having a horizontal portion that is placed on a seat body of the seat and a vertical portion that abuts on a front end of the seat body.

20. The apparatus according to claim 19, wherein the seat side attachment further includes a lower engaging member that engages with a lower surface of the seat body of the seat so that one end of the depressing force generator is fixed to the seat by holding the seat body between the horizontal portion of the seat engaging member and the lower engaging member while the vertical portion of the seat engaging member abuts on the front end of the seat body.

21. The apparatus according to claim 20, wherein the seat-side attachment further includes a clamp load adjustment that adjusts a clamp load applied to the seat body, the seat-side attachment being operable by the vehicle operator who is seated on the seat.

22. The apparatus according to claim 11, wherein:
the depressing force generator has a spherical portion formed on the second end to be connected to the control member;
the control-member-side attachment includes a socket that receives the spherical portion, and a mounting member that mounts the socket to the control member so that the depressing force is transmitted from the socket to the control member.

23. The apparatus according to claim 22, wherein the mounting member includes an abutting member that abuts on a force receiving surface of the control member to be pressed such that a load detector is compressed between the abutting member and the socket.

24. The apparatus according to claim 23, wherein the control-member-side attachment includes a base member that supports the socket such that the depressing force is allowed to be transmitted from the socket to the control member, and a holding plate that is fixed to the base member and prevents the spherical portion from coming off the socket.

25. The apparatus according to claim 24, wherein the holding plate deforms when a force equal to or greater than a predetermined value is exerted in a direction in which the spherical portion comes off the socket so as to allow the spherical portion to come off the socket.

26. The apparatus according to claim 9, wherein the actuator is able to adjust a direction of depressing a force receiving surface of the control member to be pressed prior to automatic operation of the control member by the actuator.

27. The apparatus according to claim 9, further comprising a load detector disposed at the second end of the actuator, the load detector being operable to detect a depressing load applied to the force receiving surface of the control member by the second end of the actuator.

28. The apparatus according to claim 9, wherein the actuator is capable of generating a force to drive the second end in a direction in which the control member is depressed and in a direction reverse to the direction in which the control member is depressed.

29. The apparatus according to claim 9, further comprising an adjustment that adjusts a state in which the first end of the actuator is fixed to the seat, the adjustment being operable by the vehicle operator who is seated on the seat.

30. The apparatus according to claim 9, further comprising an attachment mounted on the second end of the actuator to be fixed to the control member, the attachment being operable to disconnect the second end of the actuator from the control member when a force equal to or greater than a predetermined value is exerted between the control member and the second end of the actuator in a direction such that the control member moves apart from the second end of the actuator.

31. The apparatus according to claim 9, further comprising a releasable coupling that disconnects the first end of the actuator from the seat and disengages the second end of the actuator from the control member, the releasable coupling being operable by the vehicle operator who is seated on the seat.

32. The apparatus according to claim 9, wherein the control member comprises a braking control member.

* * * * *